United States Patent [19]

Goetz et al.

[11] 4,282,238
[45] Aug. 4, 1981

[54] INSECTICIDAL PROCESS

[75] Inventors: Norbert Goetz, Worms; Anna Steimmig; Bernd Zeeh, both of Ludwigshafen; Heinrich Adolphi, Limburgerhof, all of Fed. Rep. of Germany

[73] Assignee: BASF Aktiengesellschaft, Fed. Rep. of Germany

[21] Appl. No.: 60,836

[22] Filed: Jul. 26, 1979

Related U.S. Application Data

[62] Division of Ser. No. 952,802, Oct. 19, 1978, abandoned.

[30] Foreign Application Priority Data

Nov. 9, 1977 [DE] Fed. Rep. of Germany ....... 2750031

[51] Int. Cl.³ ............................................. A01N 43/50
[52] U.S. Cl. ................................ 424/273 R; 542/470; 548/335
[58] Field of Search .................... 424/273 R; 542/470; 548/335

[56] References Cited

U.S. PATENT DOCUMENTS

| 2,404,300 | 7/1946 | Kyrides et al. ..................... 548/335 |
| 3,531,494 | 9/1970 | Adolphi et al. ................. 548/335 X |
| 3,991,201 | 11/1976 | Heeres et al. ..................... 424/273 R |

FOREIGN PATENT DOCUMENTS 2202016 11/1972 Fed. Rep. of Germany .
1364312 8/1974 United Kingdom .

Primary Examiner—Richard Raymond
Attorney, Agent, or Firm—Keil & Witherspoon

[57] ABSTRACT

Insecticidal agents containing, as active ingredients, imidazole derivatives or salts thereof. The imidazole derivatives have the formula

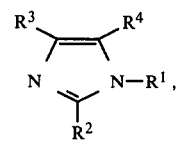

where $R^1$ denotes branched alkyl of 6 to 20 carbon atoms, linear alkyl of 6 to 16 carbon atoms, branched alkenyl of 10 to 20 carbon atoms, linear or branched alkynyl of 3 to 6 carbon atoms, 2-methyl-3-phenylpropyl or 2-methyl-3-phenylpropen-2-yl, phenyl being unsubstituted or mono- or polysubstituted by halogen or alkyl of 1 to 10 carbon atoms, and $R^2$, $R^3$ and $R^4$ denote hydrogen or methyl.

These insecticidal agents are suitable as growth regulators and ovicides for controlling insects from the Lepidoptera, Coleoptera, Diptera, Hymenoptera, Heteroptera, Homoptera and Isoptera classes.

2 Claims, No Drawings

INSECTICIDAL PROCESS

This is a division of application Ser. No. 952,802 filed Oct. 19, 1978, now abandoned.

The present invention relates to insecticidal agents containing, as active ingredients, imidazole derivatives or salts thereof, and to new imidazole derivatives.

British Pat. No. 1,148,103 discloses that imidazoles and their salts are suitable for synergizing the action of insecticidal active ingredients such as pyrethrins, carbamates and phosphoric acid esters. The imidazoles disclosed therein have a very poor insecticidal action, if at all, on representatives of the Coleoptera and Diptera orders; they act exclusively as synergists.

We have now found that insecticidal agents containing imidazole derivatives of the formula

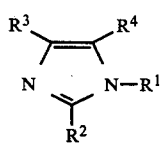

where $R^1$ denotes branches alkyl of 6 to 20 carbon atoms, linear alkyl of 6 to 16 carbon atoms, branched alkenyl of 10 to 20 carbon atoms, linear or branched alkynyl of 3 to 6 carbon atoms, 2-methyl-3-phenylpropyl or 2-methyl-3-phenylpropen-2-yl, phenyl being unsubstituted or mono- or polysubstituted by halogen or alkyl of 1 to 10 carbon atoms, and $R^2$, $R^3$ and $R^4$ denote hydrogen or methyl, or salts of these imidazole derivatives, are suitable for controlling insects from the Lepidoptera, Coleoptera, Diptera, Hymenoptera, Heteroptera, Homoptera and Isoptera classes. They interfere with the hormonal system of the animal organism, blocking or delaying the transformation to the imago, the laying of hatchable eggs and the hatching of normal eggs.

Effective insecticides of this kind, which are termed juvenile hormones, are imidazoles of the formula I in which $R^1$ denotes branched alkyl of 6 to 20 carbon atoms, especially 10 to 20 carbon atoms, linear alkyl of 6 to 16 carbon atoms, especially 10 to 14 carbon atoms, branched alkenyl of 10 to 20 carbon atoms, especially 10 to 15 carbon atoms, or linear or branched alkynyl of 3 to 6 carbon atoms, and $R^2$, $R^3$ and $R^4$ are hydrogen or methyl. Suitable juvenile hormones are also imidazoles only substituted in the 1-position and in which $R^1$ denotes 2-methyl-3-phenylpropyl or 2-methyl-3-phenylpropenyl, where phenyl is unsubstituted or mono- or polysubstituted, preferably in the 4- and 2,4-positions, by halogen, especially chlorine, or alkyl of 1 to 10 carbon atoms, especially 1 to 5 carbon atoms.

Very effective imidazoles are for instance those in which $R^2$ denotes hydrogen or methyl, $R^3$ and $R^4$ denote hydrogen, and $R^1$ denotes branched alkyl or alkenyl with isoprene structure and 10 to 20 carbon atoms, especially 10 to 15 carbon atoms, such as 3,7-dimethyloctyl, 1,5,9-trimethyldecyl, 3,7,11-trimethyldodecyl, 3,7-dimethylocta-2,6-dienyl, and 3,7,11-trimethyldodeca-2,6,10-trienyl. Imidazoles bearing in the 1-position linear alkyl of 10 to 14 carbon atoms, such as n-decyl, n-dodecyl, and n-tetradecyl, in the 2-position hydrogen, and in the 4- and 5-positions hydrogen or methyl are also very effective.

Suitable salts are salts of the imidazole derivatives with inorganic or organic acids, e.g. hydrogen halides, such as hydrochloric acid and hydrobromic acid, sulfuric acid, nitric acid, phosphoric acid, formic acid, acetic acid, propionic acid, butyric acid, acrylic acid, oxalic acid, adipic acid, lactic acid, tartaric acid, citric acid, trichloroacetic acid, stearic acid, oleic acid, phenol, perfluorooctanoic acid, p-toluenesulfonic acid and dodecylbenzenesulfonic acid.

The substituted imidazoles may be manufactured by cyclization syntheses of imidazoles by known methods, by alkylation of imidazole with the appropriate alcohols in the presence of dehydration catalysts, or with unsubstituted or substituted alkyl, alkenyl and alkynyl halides.

The following examples demonstrate the manufacture of the imidazole derivatives.

EXAMPLE 1

1-(1,5,9-trimethyldecyl)-imidazole 52.6 parts by weight of 6,10-dimethylundec-2-yl bromide and 27.2 parts by weight of imidazole are dissolved in 80 parts by weight of tetrahydrofuran and the solution is placed in a 250 ml autoclave and heated for 15 hours at 160° C. The reaction product is then filtered and the solvent is removed from the filtrate at atmospheric pressure. Distillation in vacuo of the residue obtained gives 41.5 parts by weight (83% of theory) of 1-(1,5,9-trimethyldecyl)-imidazole; b.p.: 185° C.

EXAMPLE 2

1-(3,7,11-trimethyldodeca-2,6,10-trienyl)-imidazole 72.3 parts by weight of 3,7,11-trimethyldodeca-2,6,10-trienyl chloride and 40.8 parts by weight of imidazole are dissolved in 500 parts by weight of dioxane. The reaction mixture is then refluxed for 6 hours. After the mixture has cooled it is filtered and the filtrate is concentrated in vacuo. Distillation of the residue from the filtrate under an oil pump vacuum gives 72 parts by weight (88% of theory) of 1-(3,7,11-trimethyldodeca-2,6,10-trienyl)-imidazole; b.p. (0.01 mm Hg): 155° C.

Imidazoles to be used in accordance with the invention are for example imidazoles of the formula I, in which the substituents $R^1$, $R^2$, $R^3$ and $R^4$ have the following meanings:

| No. | $R^1$ | $R^2$ | $R^3$ | $R^4$ | b.p.(°C.)/mm Hg |
|---|---|---|---|---|---|
| 1 | H$_3$C-CH(CH$_3$)-CH$_2$-CH$_2$-CH$_2$-CH(CH$_3$)-CH$_2$-CH$_2$- | H | H | H | 118/0,01 |
| 2 | H$_3$C-CH(CH$_3$)-CH$_2$-CH$_2$-CH$_2$-C(CH$_3$)=CH- | H | H | H | 124/0,01 |
| 3 | H$_3$C-CH(CH$_3$)-CH$_2$-CH$_2$-CH$_2$-CH(CH$_3$)-CH$_2$-CH$_2$-CH$_2$-CH(CH$_3$)-CH$_2$-CH$_2$- | H | H | H | 185/4 |

-continued

| No. | R¹ | R² | R³ | R⁴ | b.p.(°C.)/mm Hg |
|---|---|---|---|---|---|
| 4 | (CH₃)₂CH-CH₂-CH₂-CH(CH₃)-CH₂-CH₂-CH(CH₃)-CH₂-CH₂- (isoprene-branched alkyl) | H | H | H | 140/0,01 |
| 5 | (CH₃)₂C=CH-CH₂-CH₂-C(CH₃)=CH-CH₂-CH₂-C(CH₃)=CH- (isoprene-branched alkenyl) | H | H | H | 155/0,01 |
| 6 | i-C₃H₇-C₆H₄-CH(CH₃)-CH₂- | H | H | H | 144/0,1 |
| 7 | i-C₃H₇-C₆H₄-C(CH₃)=CH- | H | H | H | 158/0,2 |
| 8 | tert.-C₄H₉-C₆H₄-CH(CH₃)-CH₂- | H | H | H | 155/0,1 |
| 9 | tert.-C₄H₉-C₆H₄-C(CH₃)=CH- | H | H | H | 169/0,1 |
| 10 | Cl-C₆H₄-C(CH₃)=CH- | H | H | H | 165/0,1 |
| 11 | 2,4-Cl₂-C₆H₃-C(CH₃)=CH- | H | H | H | 164/1 |
| 12 | n-C₁₄H₂₉ | H | H | H | 164/1 |
| 13 | n-C₁₃H₂₇ | H | H | H | 170/4 |
| 14 | n-C₁₂H₂₅ | H | H | H | 149–152/1 |
| 15 | n-C₁₀H₂₁ | H | H | H | 135/2 |
| 16 | C₉H₁₉ | H | H | H | 175/12 |
| 17 | n-C₁₂H₂₅ | H | CH₃ | CH₃ | 170/2 |
| 18 | CH₃-C(CH₃)₂-CH₂-CH₂- | H | H | H | 121/9 |
| 19 | HC≡C-CH₂- | H | H | H | 76-78/0.6 |
| 20 | (CH₃)₂CH-CH₂-CH₂-CH(CH₃)-CH₂-CH₂-CH(CH₃)-CH₂-CH₂- | CH₃ | H | H | 126/0.1 |
| 21 | HC≡C-CH(CH₃)- | H | H | H | |
| 22 | H₃C-C≡C-CH₂- | H | H | H | |
| 23 | H₃C-CH₂-CH₂-CH(C₂H₅)- | H | H | H | |
| 24 | H₃C-(CH₂)₄-CH(CH₃)- | H | H | H | |
| 25 | H₃C-CH(CH₃)-CH₂-CH(i-C₄H₉)- | H | H | H | |
| 26 | H₃C-CH₂-CH₂-CH(n-C₃H₇)- | H | H | H | |
| 27 | H₃C-(CH₂)₃-CH(CH₃)-CH(CH₃)- | H | H | H | |
| 28 | H₃C-CH₂-CH(C₂H₅)-(CH₂)₂-CH(CH₃)- | H | H | H | |
| 29 | H₃C-(CH₂)₃-CH(C₂H₅)- | H | H | H | |
| 30 | H₃C-(CH₂)₅-CH(CH₃)- | H | H | H | |
| 31 | H₃C-CH₂-CH(C₂H₅)-(CH₂)₂-CH(C₂H₅)- | H | H | H | |
| 32 | H₃C-(CH₂)₃-CH(C₂H₅)-(CH₂)₂-CH(CH₃)- | H | H | H | |
| 33 | H₃C-CH(CH₃)-CH₂-CH(CH₃)-CH₂-CH(i-C₄H₉)- | H | H | H | |
| 34 | H₃C-CH₂-CH(C₂H₅)-(CH₂)₂-CH(i-C₄H₉)- | H | H | H | |
| 35 | H₃C-(CH₂)₃-CH(C₂H₅)-(CH₂)₂-CH(C₂H₅)- | H | H | H | |
| 36 | H₃C-(CH₂)₃-CH(C₂H₅)-(CH₂)₂-CH(i-C₄H₉)- | H | H | H | |
| 37 | H₃-C(CH₃)₂-CH₂-CH(CH₃)-(CH₂)₂- | H | H | H | |
| 38 | H₃C-(CH₂)₃-CH(CH₃)- | H | H | H | |
| 39 | H₃C-(CH₂)₄-CH(CH₃)- | H | H | H | |
| 40 | H₃C-(CH₂)₉-CH(CH₃)- | H | H | H | |
| 41 | H₃C-(CH₂)₂-CH(n-C₃H₇)- | H | H | H | |
| 42 | H₃C-(CH₂)₈-CH(CH₃)- | H | H | H | |
| 43 | n-C₆H₁₃ | H | H | H | |
| 44 | n-C₇H₁₅ | H | H | H | |
| 45 | n-C₈H₁₇ | H | H | H | |
| 46 | n-C₁₁H₂₃ | H | H | H | |
| 47 | n-C₁₆H₃₃ | H | H | H | |
| 48 | H₃C-(CH₂)₅-CH(C₄H₉)-CH₂- | H | H | H | |
| 49 | H₃C-(CH₂)₉-CH(CH₃)-CH₂- | H | H | H | |
| 50 | H₃C-CH(CH₃)-CH₂-C(CH₃)₂-CH₂- | H | H | H | |
| 51 | H₃C-(CH₂)₃-CH(C₂H₅)-CH₂- | H | H | H | |

The imidazole derivatives of the formula I in which R¹ denotes branched alkyl or alkenyl with isoprene structure are new. They correspond to the formula

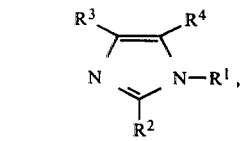

where R[1] denotes branched alkyl of 10 to 20 carbon atoms of the formula

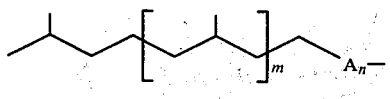

or branched alkenyl of 10 to 20 carbon atoms of the formula

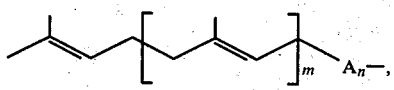

where m denotes one of the integers 1, 2, and 3, A denotes the bivalent radical —$CH_2$—$CH(CH_3)$— and n denotes one of the integers 0 and 1, R[1] further denotes 2-methyl-3-phenylpropyl or 2-methyl-3-phenylpropen-2-yl, phenyl being unsubstituted or mono- or polysubstituted by halogen or alkyl of 1 to 10 carbon atoms, R[2] denotes hydrogen or methyl, and R[3] and R[4] denote hydrogen.

The juvenile hormones of the formula I are suitable as insect growth regulators and ovicides for controlling insects from the Lepidoptera, Coleoptera, Diptera, Hymenoptera, Heteroptera, Homoptera and Isoptera classes, preferably during the embryonic, larval or pupal stage.

Examples of injurious insects from the Lepidoptera order are *Plutella maculipennis, Leucoptera coffeella, Hyponomeuta malinellus, Argyrestia conjugella, Sitotroga cerealella, Phthorimaea opercullella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarus, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar., Lymantria monacha, Pieris brassicae,* and *Aproia crataegi;* examples from the Coleoptera order are *Blitophaga undata, Melanotus communis, Limonius californicus, Agriotes lineatus, Agricotes obscurus, Agrilus sinuatus, Meligethes aeneus, Atomaria linearis, Epilachna varivestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomurum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae,* and *Pegomya hyoscyami;* examples from the Hymenoptera order are *Athalia rosae, Haplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Eriosoma lanigerum, Pemphigus bursarius, Dreyfusia nordmannianae, Dreyfusia piceae, Adelges laricis,* and *Viteus vitifolii;* an example from the Isoptera order is *Reticulitermes lucifugus.*

The agents and active ingredients according to the invention may be successfully used for crop protection and for controlling insect vectors by allowing the agents to act on the insects or their habitat. In general, the agents are employed in the same manner as conventional contact insecticides.

The active ingredients may be applied as such, in the form of formulations, or of ready-to-use application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, and strongly polar solvents such as dimethylformamide, dimethylsulfoxide, N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The amount of active ingredient in the ready-to-use formulations may vary within a wide range; it is generally from 0.0001 to 10%, preferably from 0.01 to 1%.

The active ingredients may also be successfully used in the ultra-low volume method, where it is possible to apply formulations containing up to 95% of active ingredient, or even the 100% active ingredient.

Examples of formulations are given below.

I. 3 parts by weight of 1-(3,7,11-trimethyldodeca-2,6,10-trienyl)-imidazole is intimately mixed with 97 parts by weight of particulate kaolin. A dust is obtained containing 3% by weight of the active ingredient.

II. 20 parts of 1-(3,7-dimethylocta-2,6-dienyl)-imidazole is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

III. 20 parts by weight of 1-[3-(4-isopropylphenyl)-2-methylpropen-2-yl]-imidazole is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

IV. 20 parts by weight of 1-(propyn-2-yl)-imidazole is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

There may be added to the active ingredients (if desired, immediately before use (tankmix)) oils of various types, herbicides, fungicides, other insecticides, insect pheromones and bactericides. These agents may be added to the active ingredients according to the invention in a weight ratio of from 1:10 to 10:1.

Examples of active ingredients which may be admixed are as follows:

2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyl-dimethylcarbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N',N'-dimethylformamidine, tetrachlorothiophene, O,O-dimethyl-O-(p-nitrophenyl)-phosphorothioate, O,O-diethyl-O-(p-nitrophenyl)-phosphorothioate, O-ethyl-O-(p-nitrophenyl)-phenylphosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropyl-phosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1'-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-di-n-propyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethyl-S-(2-ethylsulfynylethyl)-phosphorothioate, O,O-diethyl-S-(2-ethylthioethyl)-phosphorodithioate, O,O-dimethyl-S-(2-ethylsulfynylethyl)-phosphorothioate, O,O-diethyl-thiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethyl-phosphoroamidothioate, O,S-dimethyl-N-acetylphosphoramido-thioate, γ-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-1,4,3-benzodioxathiepine-3-oxide.

The following examples demonstrates the biological action. The comparative agent (V) is ethyl-3,7,11-trimethyldodeca-2,4-dienoate (German Laid-Open Application DOS 2,202,016). The active ingredients are numbered as in the foregoing table.

EXAMPLE A

Yellow mealworm (*Tenebrio molitor*); pupa test 2 ml of acetonic solutions of the active ingredients is administered by means of a syringe at the joint between the thorax and abdomen of yellow mealworms (*Tenebrio molitor*) which are a maximum of 24 hours old. The animals are then placed on circular filter papers in Petri dishes 10 cm in diameter.

The percentage of animals exhibiting marked deformation of the adult cuticle after ecdysis or not metamorphosing to mealworms is a measure of the effectiveness of the active ingredients.

| Active ingredient no. | Amount of active ingredient per animal (μg) | Animals with deformation of adult cuticle (%) |
| --- | --- | --- |
| 1 | 20 | 80 |
| 2 | 20 | 100 |
|   | 2 | 40 |
| 3 | 30 | 50 |

EXAMPLE B

Action on eggs of the cotton stainer (*Dysdercus intermedius*)

Approximately 100 freshly laid eggs of the cotton stainer are stuck to adhesive strips which are then dipped in aqueous solutions of the active ingredients. The strips are then kept at 25° C. and 70% relative humidity until the untreated eggs hatch.

| Active ingredient no. | Active ingredient concentration in aqueous formulation (wt %) | Kill rate (%) |
| --- | --- | --- |
| 9 | 0.05 | 80 |
| 20 | 0.1 | 100 |
| V | 0.1 | ineffective |

EXAMPLE C

Breeding experiment with cotton stainers (*Dysdercus intermedius*)

20 larvae of *Dysdercus intermedius* are bred from the 4th larval stage in 1 liter jars containing 300 g of sterilized moist sand. They are fed on cotton seeds swollen in water. In the first 2 weeks the active ingredient is added to this water; subsequently, they are fed on untreated cotton seeds. Egg laying and metamorphosis are observed.

| Active ingredient no. | Active ingredient concentration in water used for swelling (wt. %) |
| --- | --- |
| 13 | 0.1 eggs do not hatch |
| 16 | 0.1 eggs do not hatch |
| 18 | 0.1 eggs do not hatch |
| 19 | 0.1 eggs do not hatch |

A similar experiment in which the food is untreated but the sand is treated with the active ingredients gives the following results:

| Active ingredient no. | Active ingredient concentration in sand (ppm) |
| --- | --- |
| 1 | 10 eggs do not hatch |
| 2 | 5 eggs do not hatch |
| 3 | 25 eggs do not hatch |
| 7 | 25 eggs do not hatch |

EXAMPLE D

Breeding experiment with mosquito larvae (*Aedes aegypti*)

30 to 40 larvae of *Aedes aegypti* in the 4th larval stage are introduced into 200 ml of tap water to which the active ingredient formulation has been added.

The temperature at which the experiment is carried out is 25° C. Pupation and hatching of the adults are assessed, an untreated control being used for reference. During the experiment, a conventional pulverized fish food is fed once.

| Active ingredient no. | Amount of active ingredient in tap water (ppm) |
| --- | --- |
| 12 | 0.1 no adults |
| 14 | 0.25 no adults |
| 15 | 2.0 no adults |
| 17 | 2.0 no adults |
| V | 2.0 no adults |

We claim:

1. A process for controlling insects which consists essentially of applying to the insects or their habitat an effective amount of an imidazol derivative of the formula

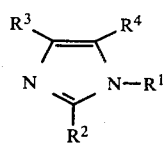 I, wherein $R^1$ denotes branched alkyl of 6 to 20 carbon atoms, linear alkyl of 6 to 16 carbon atoms, branched alkenyl of 10 to 20 carbon atoms, linear or branched alkynyl of 3 to 6 carbon atoms, 2-methyl-3-phenylpropyl or 2-methyl-3-phenylpropen-2-yl, phenyl being unsubstituted or mono- or polysubstituted by halogen or alkyl of 1 to 10 carbon atoms, and $R^2$, $R^3$ and $R^4$ denote hydrogen or methyl, or a salt of such an imidazole derivative.

2. The process of claim 1, wherein the imidazol derivative of claim 1 is allowed to act on the insects during the embryonal, larval or pupal stage.

* * * * *